United States Patent
Manaresi et al.

(10) Patent No.: US 9,914,135 B2
(45) Date of Patent: *Mar. 13, 2018

(54) METHODS AND APPARATUS FOR THE SELECTION AND/OR PROCESSING OF PARTICLES, IN PARTICULAR FOR THE SELECTIVE AND/OR OPTIMISED LYSIS OF CELLS

(75) Inventors: Nicolò Manaresi, Bologna (IT); Gianni Medoro, Casalecchio di Reno (IT); Mélanie Abonnenc, Valence (FR)

(73) Assignee: Menarini Silicon Biosystems S.p.A., Castel Maggiore (IT)

(*) Notice: Subject to any disclaimer, the term of this patent is extended or adjusted under 35 U.S.C. 154(b) by 1124 days.

This patent is subject to a terminal disclaimer.

(21) Appl. No.: 12/296,952

(22) PCT Filed: Apr. 12, 2007

(86) PCT No.: PCT/IB2007/000963
§ 371 (c)(1),
(2), (4) Date: May 1, 2009

(87) PCT Pub. No.: WO2007/116312
PCT Pub. Date: Oct. 18, 2007

(65) Prior Publication Data
US 2009/0220974 A1    Sep. 3, 2009

(30) Foreign Application Priority Data

Apr. 12, 2006 (IT) ................ TO2006A0273

(51) Int. Cl.
*B03C 5/00* (2006.01)
*B03C 5/02* (2006.01)

(52) U.S. Cl.
CPC ............ *B03C 5/005* (2013.01); *B03C 5/026* (2013.01)

(58) Field of Classification Search
None
See application file for complete search history.

(56) References Cited

U.S. PATENT DOCUMENTS 4,246,344 A * 1/1981 Silver, III ............... 435/39
6,027,488 A   2/2000 Hofmann et al.
(Continued)

FOREIGN PATENT DOCUMENTS

JP   2002536167 A   10/2002
JP   2004503775     2/2004
(Continued)

OTHER PUBLICATIONS

Cordero et al, Microelectronic J., vol. 34, pp. 1137-1142 (2003).*
(Continued)

*Primary Examiner* — Robert T. Crow
(74) *Attorney, Agent, or Firm* — Marshall, Gerstein & Borun LLP (57) ABSTRACT

Methods and apparatus for the selection or processing of particles sensitive to the application of an external stimulus, in which is produced, by applying the external stimulus, the rupture/lysis of at least one selected particle or the fusion of first and second selected particles, by means of the organization of the particles using a first field of force by selectively energizing electrodes of an array of selectable electrodes having dimensions comparable to or smaller than those of the particles, applying to the electrodes a first configuration of stresses; and by applying to the electrodes a second configuration of stresses, so as to create a second field of force, located substantially close to at least one selected particle to be lysated or to a pair of first and second particles to be fused and such as to produce the application of a stimulus suited to produce their lysis or fusion.

18 Claims, 6 Drawing Sheets

(56) References Cited

U.S. PATENT DOCUMENTS

| | | | |
|---|---|---|---|
| 6,280,586 B1 * | 8/2001 | Wolf et al. | 257/253 |
| 6,294,063 B1 | 9/2001 | Becker et al. | |
| 6,448,794 B1 | 9/2002 | Cheng et al. | |
| 6,492,175 B1 | 12/2002 | Muller et al. | |
| 6,858,439 B1 | 2/2005 | Xu et al. | |
| 6,977,033 B2 | 12/2005 | Becker et al. | |
| 7,033,473 B2 | 4/2006 | Gascoyne et al. | |
| 2002/0036141 A1 | 3/2002 | Gascoyne | |
| 2003/0104588 A1 | 6/2003 | Orwar et al. | |
| 2003/0146100 A1 * | 8/2003 | Huang et al. | 204/547 |
| 2004/0058423 A1 * | 3/2004 | Albritton | G01N 27/44743 435/173.7 |
| 2004/0191789 A1 | 9/2004 | Manaresi et al. | |
| 2004/0209354 A1 * | 10/2004 | Mathies et al. | 435/287.2 |
| 2004/0211669 A1 | 10/2004 | Cummings | |
| 2004/0224397 A1 * | 11/2004 | Culbertson et al. | 435/173.7 |
| 2005/0070018 A1 | 3/2005 | Johnson et al. | |
| 2005/0072677 A1 | 4/2005 | Gascoyne et al. | |
| 2005/0120402 A1 * | 6/2005 | St. John et al. | 800/21 |
| 2005/0211559 A1 * | 9/2005 | Kayyem | 204/601 |
| 2009/0220974 A1 * | 9/2009 | Manaresi | B03C 5/026 435/6.16 |

FOREIGN PATENT DOCUMENTS

| | | |
|---|---|---|
| WO | WO00/047322 | 8/2000 |
| WO | WO00/69565 | 11/2000 |
| WO | WO-01096857 | 12/2001 |
| WO | WO03/001193 | 1/2003 |
| WO | WO03/014739 | 2/2003 |
| WO | WO04/071668 | 8/2004 |
| WO | WO-2005/075656 | 8/2005 |
| WO | WO2007/049103 | 5/2007 |
| WO | WO-2007079663 A1 | 7/2007 |

OTHER PUBLICATIONS

Lu et al, Lab Chip, vol. 5, pp. 23-29 (2005).*
International Search Report for PCT/IB2007/000963 dated Sep. 28, 2007.
Office Action of JP2009-504847 dated Aug. 21, 2012 With an English Translation.
Office Action of JP2009-504849 dated Aug. 21, 2012 With an English Translation.
K. Maswiwat, et al. Electrochimica Acta. 2006. vol. 51: pp. 5215-5220. Published online May 3, 2006.
Hughes. Phys. Med. Biol., 1998, vol. 43, pp. 363-3648.
Lin et al., Lab Chip. 2004, vol. 4, pp. 104-108.

* cited by examiner

METHODS AND APPARATUS FOR THE SELECTION AND/OR PROCESSING OF PARTICLES, IN PARTICULAR FOR THE SELECTIVE AND/OR OPTIMISED LYSIS OF CELLS

TECHNICAL FIELD

The present invention concerns methods and apparatus for the selection and/or the processing of particles, in particular particles composed of cells or including cells and/or cellular material, for example for the selective and/or optimised lysis of cells, and is applied principally in the implementation of protocols with resolution on a single cell. The term "processing" of cells here and below means any type of operation that can be carried out on a single particle or cell, or on a group of them.

STATE OF THE ART

The patent PCT/WO 00/69565 to G. Medoro describes an apparatus and a method for the manipulation and identification/recognition of particles making use of closed cages with dielectrophoretic potential and possible integrated sensors. The method described teaches how to control the position of each particle independently of all the others in a two-dimensional space. The force used to trap the particles suspended in a fluid medium is negative dielectrophoresis. The individual control of the manipulating operations is achieved by the programming of memory elements and circuits associated with each element of an array of electrodes and sensors integrated in the same substratum. The device allows cells to be isolated, but requires that they be moved towards a second microchamber, fluidly isolated from the first one. Moreover, no method is contemplated for transforming the cells.

The U.S. Pat. No. 6,294,063 to Becker et al. describes a method and apparatus for the manipulation of packages of solid, liquid or gaseous biological material by means of a distribution of programmable forces. The patent also mentions the use of sensors. In this case too the isolation of the cells may take place only by moving the cells physically through the whole device.

A further force for the manipulation of particles is the force of viscous friction generated by electro-hydrodynamic flows (EHD), such as electrothermal flows (ETF) or AC electro-osmosis. In N G. Green, A. Ramos and H. Morgan, J. Phys. D: Appl. Phys. 33 (2000) the EHD are used to shift particles. For example PCT WO 2004/071668 A1 describes an apparatus for concentrating particles on electrodes, exploiting the above-mentioned electro-hydrodynamic flows.

The Italian patent application BO2005A000481, Medoro et al., lists some methods for manipulating particles with arrays of electrodes, and some methods and apparatus for identifying them.

Instead the international patent application PCT/IT02/00524 describes a method in which first biological entities may be transformed by being put in contact with second biological entities (for example liposomes containing DNA, or microbeads), where the first biological entities are immobilised on a surface defined by a matrix of first electrodes which may be at least in part selectively activated and directed, placed facing at least one second electrode, and are contacted with the second biological entities shifted by means of dielectrophoresis cages.

The patent application PCT IB 2006000636 in the name of the same Applicant concerns a method and apparatus for the characterisation and/or count of particles by means of non uniform, time variable fields of force and integrated optical or impedenziometric sensors. The fields of force may have positive or negative dielectrophoresis, electrophoresis or electro-hydrodynamic movements, characterised by a set of stable points of equilibrium for the particles (solid, liquid or gaseous); the same method is suitable for the manipulation of drops (liquid particles) exploiting known effects such as Electrowetting on dielectric, with the aim of acting on the control of the position of each particle present in the specimen, so as to shift said particles in a deterministic or statistical way, to detect their presence with the integrated optical or impedenziometric sensors, and/or to characterise their type, in order to count them or manipulate them in an efficient way.

In the Italian application in the name of the same Applicant, no. TO2006A000226 of 27.3.2006, methods and apparatus are described for the processing (for example washing, incubation, etc.) of particles in which the particles suspended in a first fluid are introduced under laminar flow conditions into at least one first microchamber or first region of the same, in which a second fluid is introduced under laminar flow conditions into at least one second region of the microchamber or of a second microchamber, in such a way as not to mix with the first fluid, and in which at least one field of force (F) acting on the particles is activated in the microchamber(s), to provoke a shift of the particles alone in a predetermined direction and to transfer the same in suspension into the second fluid; an apparatus' is preferably used including at least three microchambers arranged in sequence with each other in one direction and each connected with the microchamber immediately before it and after it with two orifices offset from each other in a direction perpendicular to the direction of sequence of the microchambers.

Recently, in the article A single cell electroporation chip, Lab on a Chip, 2005, 5 (1), 38-43, Michelle Khine, Adrian Lau, Cristian Ionescu-Zanetti, Jeonggi Seo and Luke P. Lee, it has been described how to increase the permeability of the cellular membranes by electroporation carried out on single cells; in this way, polar substances which could not otherwise permeate the plasmatic membrane (such as dyes, medicines, DNA, proteins, peptides and amino acids) can be introduced into the cell.

The article Flow-through micro-electroporation chip for high efficiency single-cell genetic manipulation, Sensors and Actuators A: Physical. Volume 104, Issue 3, 15 May 2003, Pages 205-212, Yong Huang, Boris Rubinsky describes in particular the genetic manipulation of individual cells, which is of great interest in fields such as biology and biotechnologies, obtained by means of an electroporation chip which makes use of micro-fluid channels to manipulate single cells with precision; as is known, electroporation is a technique that uses intense electrical fields to induce structural re-arrangements in the cell membrane; pores are thus formed through the membrane when the transmembrane potential exceeds the dielectric perforation voltage of the membrane (0.2-1.5V) allowing external substances to penetrate the membrane and reach the cytoplasm that it contains.

The electroporation of single cells is an interesting technique also because it allows the study of the variations that occur in a cell population cell by cell, and also the study of the intracellular chemistry, for example supplying specific phenotypes to individual cells by activating or blocking the expression of specific and individual proteins. Using technology based on the use of matrices implemented on chips it is therefore possible to produce apparatus for HTS testing (high throughput screening), linked both to the expression of DNA and proteins and to chemical compounds (for example medicines) which are directed towards specific cell targets (for example receptors).

The electroporation of single cells is also an advantageous technique in comparison with the protocols of electroporation in bulk that are normally used, which require very high voltages (>103 V) and do not allow an efficacious control of the permeability of the individual cells, so that, for example, it is difficult to reclose the pores opened previously.

The attempts made so far to achieve the electroporation of single cells range from the use of carbon fibre microelectrodes (Lundqvist et al., 1998) to other techniques such as capillaries filled with electrolyte, micropipettes, and micromanufactured chips.

Micromanufactured devices are ideal both for isolating single cells and for focussing the electric field.

Lastly, the article "Controlling cell destruction using dielectrophoretic forces", A. Menachery and R. Pethig, IEE Proc.-Nanobiotechnol., Vol. 152, No. 4, August 2005, reports on a study of the lysis of cells for different types of cells in castellated or polynomial electrodes, and proposes the differential lysis of cells of different types present in a mixture (choosing frequencies and amplitudes such as to lysate one type, but save another).

However, as the electrodes are much bigger than the cells, it is not proposed to use this approach, and probably it is not possible to use it, to destroy single cells selectively, irrespective of their type. In fact, since the position with respect to relatively large electrodes (and consequently the intensity of the field to which they are subjected) varies considerably, this method cannot work homogeneously on the various cells.

Lysis is preferably induced using fields in an interval of frequencies between the cross-over frequency (beyond which the cells pass from negative dielectrophoresis (nDEP) to positive (pDEP)), and lower than the frequency beyond which the potential of the membrane is attenuated due to the exceeding of the membrane relaxation constant.

SUMMARY OF THE INVENTION

The aim of the present invention is to supply methods for operating on fluid samples containing particles, typically cells, for carrying out the purification and/or isolation of single cells and/or the transformation of one or more cells, which is without the limitations and/or the inconveniences described for the prior art.

In particular an aim of the present invention is to act on the control of the position of each particle present in the sample, in order to shift said particles in a deterministic way, to operate selectively on each cell and/or perform in a more efficacious way operations such as lysis, fusion, etcetera.

Here and below, the terms "particles" or "particle" are used to indicate micrometric or nanometric entities, natural or artificial, such as cells, subcellular components, viruses, liposomes, niosomes. The term cell will sometimes be used, but where not specified otherwise it must be understood as a non limiting example of the use of particles in the sense described more fully above.

The present invention therefore concerns the methods as specified in the claims 1, 11, 12, 13, 15.

The invention also concerns an apparatus as specified in claim 17.

In particular, non uniform, time variable fields of force are used and integrated optical sensors. The fields of force may have positive or negative dielectrophoresis, electrophoresis or electro-hydrodynamic movements, characterised by a set of stable points of equilibrium for the particles.

In this way the limitations of the prior art are overcome by the present invention.

The implementation of the methods according to the invention allows the accurate purification of a sample of cells even from contaminating agents present in a low percentage. It also allows cells to be transformed efficaciously and selectively with the introduction of genetic material. Lastly it allows a few interesting cells to be rapidly isolated from a heterogeneous sample.

Further characteristics and advantages of the invention will be clear from the following description of some of its non limiting embodiments, with reference to the figures in the attached drawings.

DETAILED DESCRIPTION

The aim of the present invention is to carry out methods and apparatus for the manipulation and/or separation and/or analysis of particles.

The methods of the invention are based (FIG. 1) on the use of a non uniform field of force (F) with which to attract single particles or groups of particles (CELL) towards positions of stable equilibrium (CAGE). This field may be, for example, a field of dielectrophoresis (DEP), negative (NDEP) or positive (PDEDP), or a field of electrohydrodynamic movements (EHD).

The processing carried out on the cells is based on the application of localised electric fields able to provoke the permanent rupture of the cellular membrane, or the fusion of two particles.

The method may also make use of integrated sensors, preferably of the optical and/or impedenziometric type, for example in all those steps in which it is necessary to check the type of particles close to certain electrodes. Alternatively, similar information may be available by means of non integrated optical sensors, coupled to a microscope, which allows the examination of the contents of the microchamber in which the methods of the invention are being carried out.

Generation of Forces

There are various methods for generating forces to shift particles, according to the prior art, by means of arrays of electrodes (EL), formed on a substratum. Typically, according to previous patents of the same Applicant (FIG. 1), a cover (LID) is used, which may in turn be an electrode, which delimits a microchamber, in which are the particles (CELL), typically suspended in a fluid composed of a liquid. In the case of dielectrophoresis (DEP), the voltages applied are periodic in-phase voltages (Vphip) indicated with the plus sign (+) and counterphase voltages (Vphin) indicated with the minus sign (−). The term "counterphase voltages" means voltages offset by 180°. The field generates a force which acts on the particles of a region of space (CAGE), attracting them towards a point of equilibrium (PEQ). In the case of negative DEP (NDEP), it is possible to produce closed force cages, according to the prior art, if the cover (LID) is a conductive electrode; in this case the point of equilibrium (MPEQ) corresponds to each electrode connected to Vphin (−) if the adjacent electrodes are connected to the opposite phase Vphip (+) and if the cover (LID) is connected to the phase Vphin (−). This point of equilibrium (MPEQ) is normally at a distance in the liquid with respect to the electrodes, so the particles (CELL) are in levitation, in a stationary state.

Figure 1:
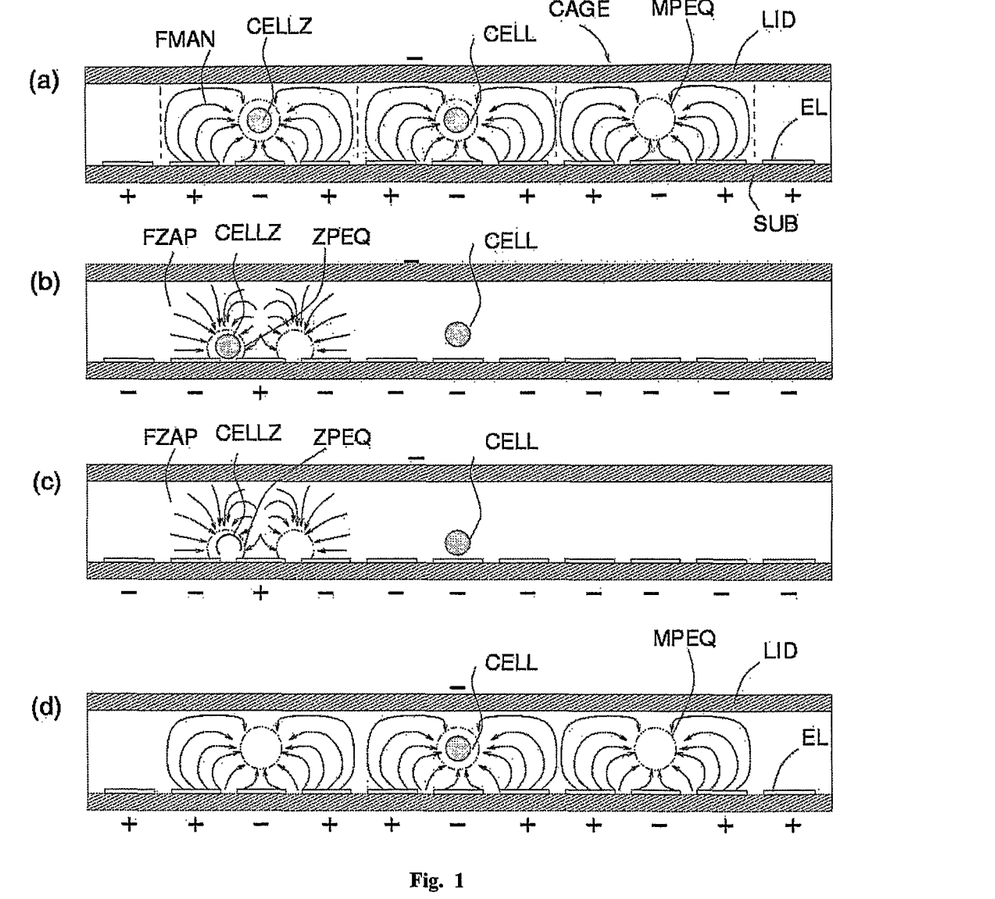
FIG. 1 schematically illustrates the steps of a first method according to the invention carried out in a manipulation apparatus illustrated in section in elevation.

In the case of positive DEP (PDEP) the point of equilibrium (ZPEQ) is normally at the surface on which the electrodes are realised, and the particles (CELL) are in contact with it, in a stationary state. For the PDEP it is not necessary to have further electrodes in the cover, because the points of equilibrium of the PDEP correspond to the maximums of the electric field. For the electro-hydrodynamic movements (EHD), the configurations of electrodes generate flows which push the particles towards the minimum points of the flow.

For the sake of simplicity, below is considered purely as an example, and therefore without limitation for the purposes of the present invention, the use of closed cages with negative dielectrophoresis as the activating force for the steps of particle movement in the description of the methods and apparatus (for which it is necessary to use a cover acting as an electrode) of the invention. To experts of the sector with ordinary abilities it is clear that it is possible to generalise the methods and apparatus described below for the use of different activating forces, and different types of particles.

Method for the Selective Lysis of Particles

The particles to be lysated are positioned close to the gap between two electrodes by one of the above mentioned actuation forces, energising the electrodes with sinusoidal voltages of a first amplitude (MA) and frequency (MF). The gap is preferably smaller than 10 μm, and typically around 1-3 μm, so that a low voltage stimulus, compatible with the supply voltage of an integrated circuit (e.g. 2.5, 3.3 or 5 V), is enough to determine a transmembrane potential sufficient to cause the irreversible rupture of the particle.

This stimulus is preferably composed of a train of sinusoidal impulses of a second amplitude (ZA) and a second frequency (ZF).

Electric impulses are applied between the two selected electrodes so as to provoke the lysis of the cell.

FIG. 1 shows in section the evolution over time of the fields of force and of the "patterns" (that is the complex of configurations of (+) or (−) state of the electrodes) of the voltages applied to the electrodes, according to a preferential embodiment of the invention. In FIG. 1(a), the cells (CELL) are in nDEP, suspended in the liquid in a first point of equilibrium (MPEQ). In FIG. 1(b) the pattern of voltages applied to the electrodes (EL) changes, so the frequency and optionally the amplitude of the voltages applied, as well as the force to which the cells are subjected, change to pDEP (FZAP). However, thanks to the change of the pattern of voltages, only the cell to be lysated (CELLZ) is subjected to a significant force, so it is attracted towards a new point of stable equilibrium (ZPEQ). Near that point the electric field is maximum and the frequency is such that a sufficient transmembrane potential to lysate the cell is provoked.

Figure 2:
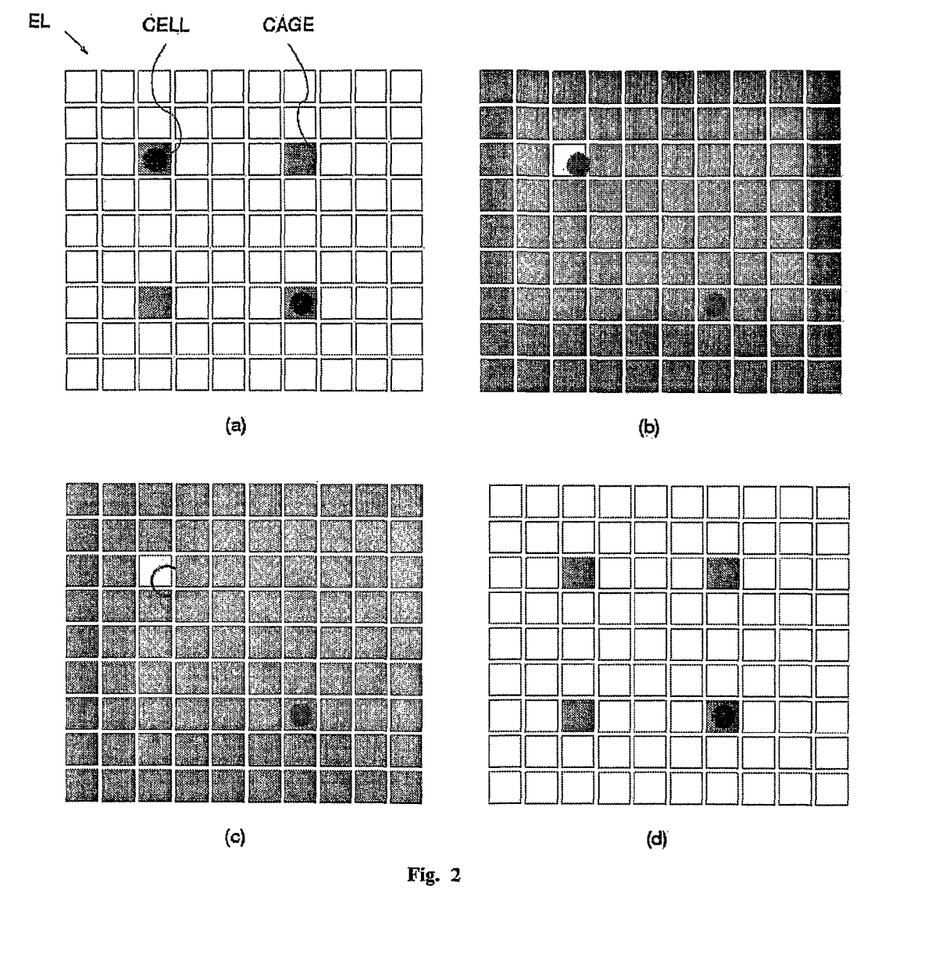
FIG. 2 illustrates the steps of the method in FIG. 1 carried out with the same apparatus as in FIG. 1, but illustrated in layout viewed from above.
Figure 3:
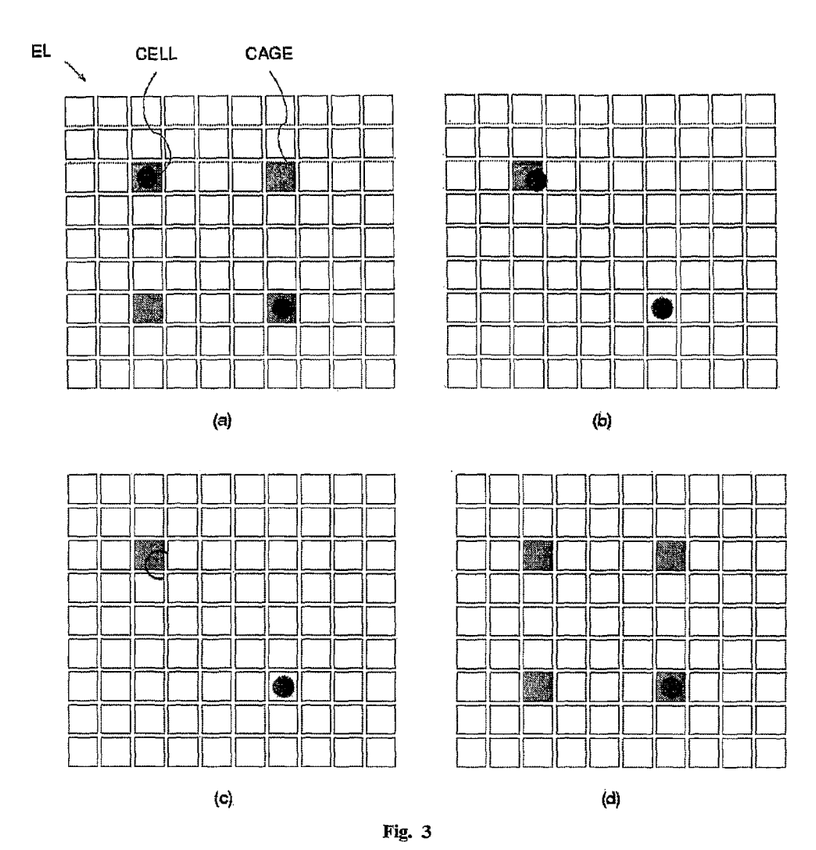
FIG. 3 illustrates in the same view as FIG. 2 a possible variation of the method in FIGS. 1 and 2.

FIG. 2 shows in layout the configurations of electrodes for the same steps (a)-(d) as FIG. 1, where the pattern of electrodes in phase and counterphase with the voltage applied to the lid is indicated by the colour (in phase grey, in counterphase white).

This sequence of patterns is particularly favourable since, during lysis, the other cells in neighbouring areas are subjected to an almost null electric field, as both the cover and the electrodes are in phase. If the amplitude of the voltage applied to the cover is equal to the amplitude of the voltage applied to the electrodes, the field on those cells is null.

Alternatively, the series of patterns shown in FIG. 3(a)-3(d) may be adopted. In this case, as is shown by the number of electrodes in phase and counterphase represented by the colours white and grey, the advantage lies in the need to reprogramme a smaller number of electrodes each time, which may be advantageous if the process of writing the memory cells for the pattern of electrodes to be actuated is slow. Otherwise it is generally preferable to adopt the previous solution in FIG. 2.

With sensors integrated in the array of electrodes that delimit the bottom surface of the microchamber, for example of optical type, it is easy to check when lysis has occurred, using the methods described in the above-mentioned international patent application no. PCT IB 2006000636 of the same Applicant, to see whether the cage corresponding to the lysated cell is still full or empty, or better to check for the presence of debris resulting from lysis.

Substantially, with the methods described it is possible to select or process particles sensitive to the application of an external stimulus using a method comprising in general the step of producing, by applying said external stimulus, the rupture or lysis of at least, one selected particle; and wherein are also contemplated the steps of:

a) bringing the particles (CELL) close to electrodes (EL) of an array of selectable electrodes having dimensions comparable to or smaller than those of said particles, to which may be applied a first pattern (PMAN) of tensions to organise optionally, if necessary, said particles (CELL) by means of a first field of force (FMAN), by selectively energising said electrodes (EL);

b) applying to the electrodes a second pattern (PZAP) of voltages, so as to create a second field of force (FZAP), located substantially close to at least one selected particle to be lysated (CELL) and such as to produce the application to said at least one selected particle of a stimulus suited to produce its rupture or lysis.

The particles are suspended in a chosen fluid, in case one wants to use the passage from nDEP to pDEP as described previously to obtain lysis, so as to present a relatively low electric conductivity.

The first pattern (PMAN) of voltages for generating the first field of force (FMAN) presents a first amplitude (MA) and a first frequency (MF); and the second pattern (PZAP) of voltages for generating the second field of force (FZAP) presents a second amplitude (ZA) and a second frequency (ZF), at least one of which is different from said first amplitude (MA) and first frequency (MF). In this case, the stimulus applied to obtain lysis consists of a force that can be applied to the at least one selected particle by the second field of force (FZAP) and both the first and the second pattern of voltages are generated in AC (alternating current). In particular, the at least one selected particle is a biological entity with a lysable membrane, in the examples described a cell, and the stimulus applied consists of bringing the transmembrane potential of the at least one selected particle to a value such as to produce the rupture of the membrane.

According to a possible variation of the method of the invention, which may be considered illustrated in FIG. 2(b), the stimulus applied to the selected particle to lysate it consists vice versa of heating located in the fluid in which is suspended the selected particle to be lysated.

According to this possible variation, particularly advantageous if the particles are suspended in a fluid (liquid) presenting a high electric conductivity (for example physiological solution), the second pattern (PZAP) of voltages is such as to produce the selective heating by Joule effect of those selected electrodes in the array of electrodes with which the second field of force (FZAP) is generated, in FIG. 2(b) the electrode shown in white, on which the whole current supplied to the device illustrated is practically concentrated.

In this case it is clear that at least the second pattern of voltages may be generated in either AC or DC (direct current).

Anyway, the methods described according to the invention include a step of checking the lysis of the at least one selected particle, preferably carried out by means of the already mentioned sensors integrated with the array of electrodes, in a single chip.

Lastly, according to a further possible variation of the methods described, if one is interested in selectively recovering the debris produced by lysis, after the step b) described above, the following steps may be carried out:

c) applying said first pattern (PMAN) of voltages to the electrodes again; and d) while step c) is in progress, producing a slow and controlled shift of the fluid to recover a selected product of lysis of the at least one selected particle.

In fact, as is well known to experts in the field, in the case of actuating the movement of the particles by dielectrophoresis, the forces acting on the particles due to the applied field are in proportion to the cube of the radius of the particles, while the forces of hydrodynamic viscous friction are in proportion only to the radius of the particles; therefore the smallest particles (the debris of lysis in this specific case) may be carried along by a moderate flushing of the fluid in which the particles are suspended, while the largest particles (the non lysated cells) are kept in a stationary position (against the viscous flushing action) by the nDEP cages positioned in stationary mode and in which the cells are trapped.

Figure 4:
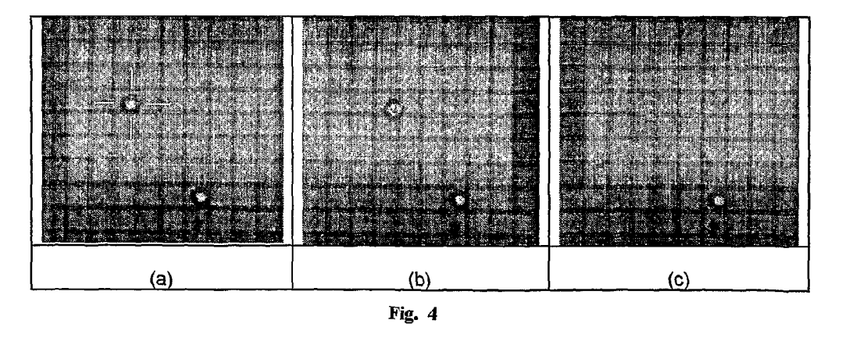
FIG. 4 illustrates the actuation of the method in FIG. 1 with a photographic sequence.

The efficacy of the methods described, in particular of the method according to the FIGS. 1 and 2, is shown in FIG. 4. Two Raji cells suspended in an aqueous solution with Mannitol 280 mM (millimolar) and KCl 6.25 mM are organised, see FIG. 4(a), by the electric field (MF) applied (MA) in which the electrodes in the array have sinusoids with a peak-peak amplitude of 3.3 V, the conductive cover (LID) an amplitude of 6.6V, all with frequency 50, kHz. The cells are taken onto the in-phase electrodes with the lid surrounded by electrodes of the opposite phase (offset by 180°).

After that, the pattern of the voltages applied to the electrodes varies, putting into counterphase also the electrode on the cell at bottom right, which must be preserved. Although there is no cage, the cell remains in the same position, due to inertia. Instantaneously, the applied electric field changes so as to produce positive dielectrophoresis (FZAP), bringing the frequency of the electric field (ZF) to 400 kHz, and the particle still present in the cage (CELLZ) goes into a new point of stable equilibrium due to the force of positive dielectrophoresis, now generated by the field, which is on the gap between the electrodes, see FIG. 4(b). That region corresponds to the maximums of the electric field, which at that frequency are sufficient to provoke the lysis of the membrane, see FIG. 4(c).

Figure 5:
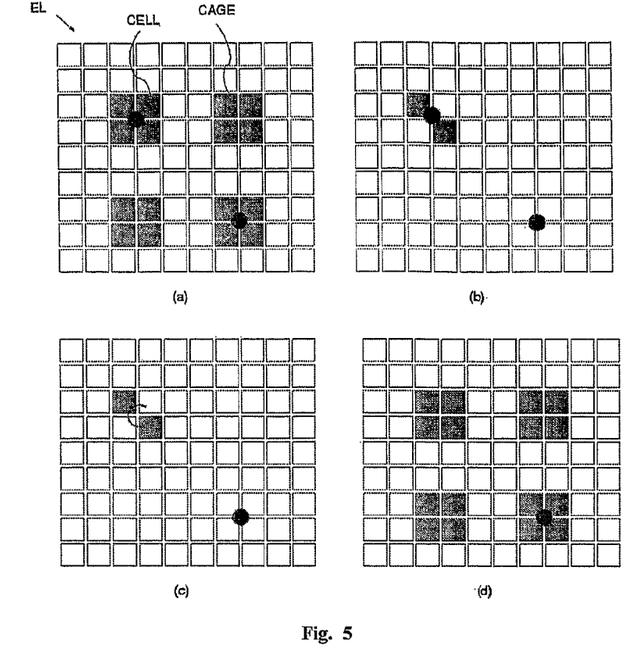
FIG. 5 illustrates in the same view as FIG. 2 a further variation of the method in FIG. 1.

It appears clear to experts in the sector with ordinary abilities that the electric field may be varied, in different ways, in particular also (or only) in amplitude, or the initial pattern of electrodes for manipulation and lysis may be chosen differently, for example as in FIG. 5.

In this case, it starts from a nDEP pattern, FIG. 5(a), which positions the particles in a point of equilibrium (MPEQ) lying vertically to the point of equilibrium for the pDEP (ZPEQ), for the next pattern of electrodes. In this way the selected cell does not move from its vertical line, and the lysis process can be accelerated because the cell takes less time to reach the area of maximum electric field in which lysis takes place.

Method for Particle Fusion Assisted by Dielectrophoretic Manipulation

Figure 6:
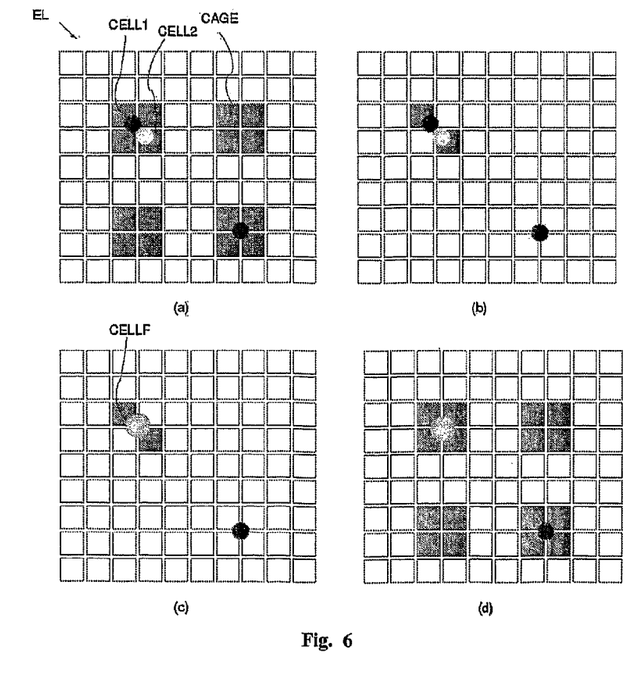
FIG. 6 illustrates in the same view as FIG. 2 a further method of the manipulation of particles according to the present invention.

In this case, two particles are brought into contact in the same point of stable equilibrium (MPEQ) by the force (F) generated by the electrodes (EL). The stimulus that is applied next to the pair of cells in contact is chosen with an amplitude and frequency such as to provoke a fusion of the two cellular membranes into a single entity (FIG. 6).

With sensors integrated in the chip that holds the array of electrodes, for example of an optical type, it is then possible to check that fusion has taken place without the need of an external microscope.

Applications of fusion include for example the generation of hybrids, of both eucariot cells and bacteria, or of plants.

For example, one could consider the possibility of using a similar method to reprogramme differentiated cells towards stem cells, for example combining a differentiated cell with an enucleated stem cell.

So, according to this method, the fusion of first particles with second particles is produced, in which the first and second particles are biological entities with a lysable membrane, for example cells or micro-organisms, and in which the membrane of the particles is sensitive to the application of an external stimulus, performing the steps of:

a) bringing said first and second particles (CELL) close to electrodes (EL) of an array of selectable electrodes having dimensions comparable to or smaller than those of said particles, to which may be applied a first pattern (PMAN) of tensions to organise optionally, if necessary, said first and second particles (CELL) by means of a first field of force (FMAN), by selectively energising said electrodes (EL);

b) applying to the electrodes a second pattern (PZAP) of voltages, so as to create a second field of force (FZAP), located substantially close to at least one first and one second selected particles to be fused together and such as to produce the application to the same of a stimulus suited to produce the fusion of the membranes of the first and second selected particles.

Method of Isolating Cells by Survival

A multiplicity of cells is flushed in suspension in the microchamber with the array of electrodes. Using integrated sensors (for example optical and/or impedenziometric) and/or external sensors (for example an optical sensor coupled to a microscope, with or without fluorescence), the type or cell found in each point of equilibrium (PEQ) is identified. Stimuli for lysis are then applied selectively to all the cells that are not interesting, preserving the vitality of the neighbouring interesting cells.

The sample is then flushed out, recovering the interesting live cells and the lysate of non interesting cells.

According to the description, a method is therefore carried out for isolating interesting particles from a population of particles including the interesting particles, characterised in that it comprises the following steps:

a) introducing the population of particles, suspended in a fluid, into a microchamber, where the microchamber is provided with an array of selectable electrodes;
b) applying to said population of particles the method of selective lysis described above to produce the selective lysis of all the particles of the population except the interesting ones;
c) recovering the interesting particles.

Step b), particularly in the case where the position of the interesting particles with respect to the array of electrodes is not known a priori and the interesting particles possess characteristics such as to be sensitive only to a determined intensity and/or type of stimulus (also not known a priori), is applied simultaneously and/or repeatedly to all the particles of the particle population by applying to said electrodes a plurality of voltage patterns suited to apply to said particles stimuli of an intensity and/or type such as to produce, in this way, the selective lysis of all the particles in the particle population except the interesting ones.

The different type may for example include the application of AC voltages with determined frequencies, known to be ineffective in the lysis of the interesting particles, but to be efficacious for the lysis of the remaining particles. The different intensity may for example be a growing intensity.

With respect to isolation based on moving the interesting cells into a second microchamber for recovery, the method described above presents the following advantages:

1. Speed of Execution

The cells move slowly under the described forces (DEP, ETF, EHD) of actuation, and the sorting based on moving the cells into a microchamber for recovery is therefore relatively slow. Vice versa, the time to complete the sorting operation based on survival requires only one cell to have reached the nearest point of stable equilibrium (PEQ), and the time of lysis of the cell (about one second), and it is not necessary to move it through the whole selection microchamber.

2. A Cooling System is not Necessary

The cells to be eliminated can be lysated in series, working by sub-regions of the microchamber. In this way it is not necessary to have cooling systems, even for working on very large chips with relatively conductive buffers, because the quantity of heat developed is proportional to the energised area, which may be made as small as one likes.

3. The Chip May have Very Large Dimensions

As it is not necessary to energise the whole chip at the same time, the problem of resistive drop on the tracks that carry the stimuli to the various electrodes is correspondingly reduced. Above all with relatively conductive buffers, and with low pitch between electrodes, the resistive drop on the tracks inside the chip and/or the drop on the conductive layer of the lid (when NDEP cages are used for actuation) is not negligible if the whole array of electrodes is energised. Energising only a part of the layer, the resistive load to be managed is limited and the voltage drop on the tracks is decreased.

4. Operation Also with Cells that Cannot be Manipulated with the Fields of Force If the electrode matrix is sufficiently dense (with dimensions comparable to or smaller than the cells), so as to be able to perform selective lysis on cells even without having selected them beforehand, the method of the invention can still be completed, in particular if the cells to be preserved, presenting different characteristics from the non interesting cells, are sensitive to stimuli carried out at different frequencies of voltages applied to the electrodes.

5. Simplified Microfluidic Package

It is not necessary to have a double microchamber, but a single compartment is sufficient, and the recovery need not be selective, so the contamination is not linked to the characteristic of the recovery flow.

Any sensors integrated in the chip will be used to
1. determine the interesting particles.
2. Check the lysis of the undesired cells.

Method of Ultra-Purification of Cells

With enrichment techniques it is often easy to eliminate cells present in proportions greater than the interesting cells by several degree of magnitude (for example with centrifugations in gradients of density or enrichment with magnetic balls, etc.). However it is sometimes difficult to eliminate the few contaminating cells that remain (for example present in a proportion of 0.1-10%) to obtain a 100% pure sample. This is required for example if one wants to cultivate the interesting cells but these proliferate less rapidly than the non interesting ones, which, even if present in a low percentage, would then prevail downstream from the proliferation.

As in the selection method described previously, the cells are introduced into the microchamber, the cells optionally line up in points of stable equilibrium near the electrodes (PEQ), and the contaminating cells are eliminated by lysating them with the electrodes, obviously after having identified them with suitable integrated or external sensors, or on the basis of intrinsic differences such as the frequency of the voltage applied to the electrodes which produces lysis.

In this case too, the integrated sensors, if they exist, can optionally be used to
1. determine the interesting particles.
2. Check the lysis of the undesired cells.

The 100% pure cells are then recovered, flushing out the sample.

Based on this aspect of the invention, a method is therefore actuated for the ultra-purification of interesting particles from contaminating particles, both contained in a population of particles, characterised in that the isolation method described above is applied, where step b) is applied only to the contaminating particles.

Method of Cell Analysis

The study at biomolecular level of DNA and/or of proteins in single cells is increasingly interesting. According to an aspect of the present invention, a method is proposed for selecting and shifting selected cells possibly from a multiplicity of cells from a first multiplicity of points, and bringing them to a second multiplicity of points of analysis of micrometric dimensions, each point of analysis comprising at the most one single cell. The cell is lysated and its content is analysed on the chip, for example according to known techniques such as PCR and/or capillary electrophoresis on chip.

Based on the invention, a method is therefore supplied for the analysis of particles, characterised in that it comprises the steps of:
a) introducing said particles, suspended in a fluid, into a microchamber;

b) shifting said particles, selectively, each into a predetermined point of analysis separate from said microchamber, but hydraulically connected to it;
c) applying to said particles present in said predetermined points of analysis a method of selective lysis as described above;
d) applying a defined analysis protocol on site to the respective debris of the lysis of said particles; where said defined analysis protocol is chosen from the group including: PCR, capillary electrophoresis on chip; combinations of the previous ones.

Cell Analysis Apparatus

Figure 7:
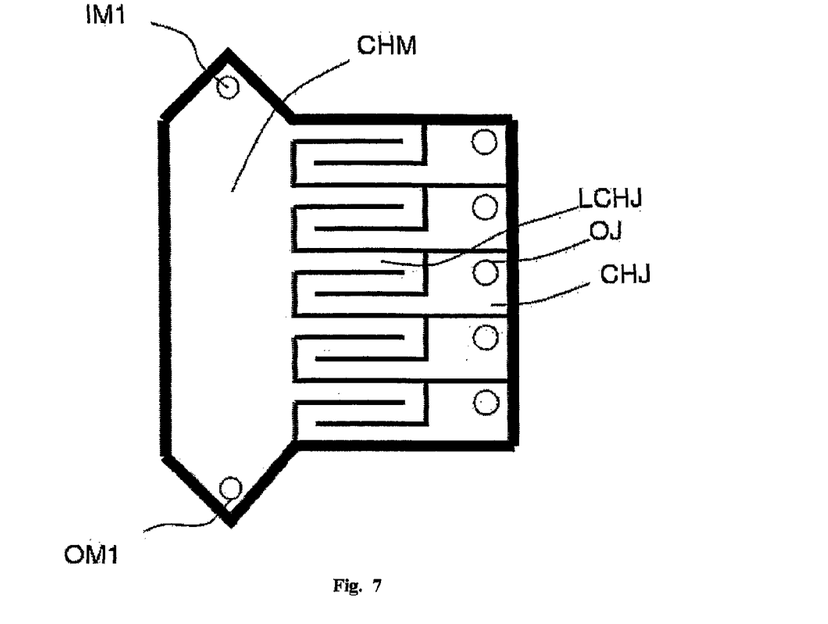
FIGS. 7 to 9 illustrate different embodiments of an apparatus for a particularly advantageous actuation of the methods of the invention.
Figure 8:
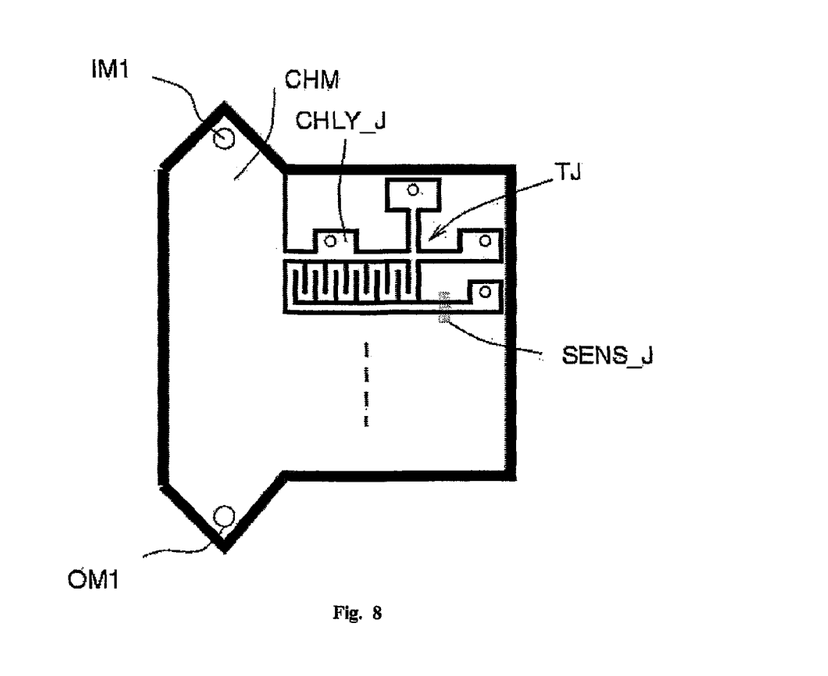
Figure 9:
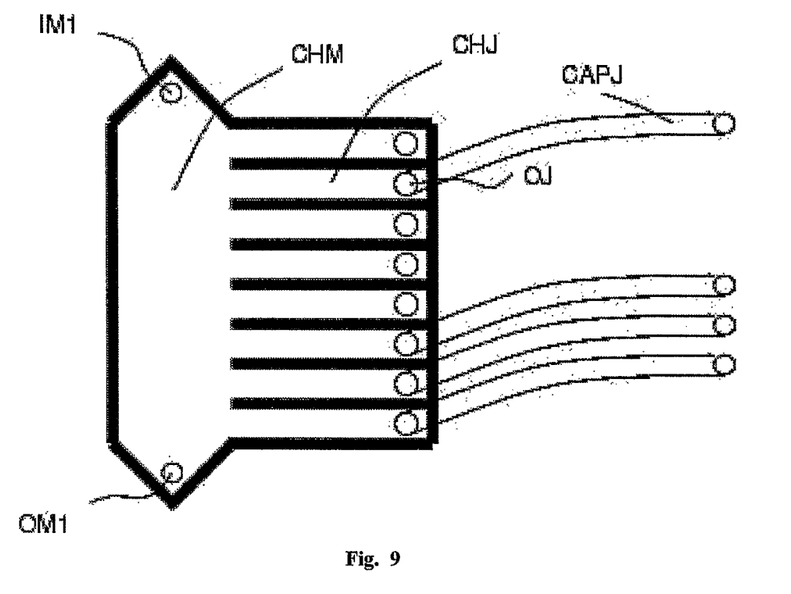

To carry out the methods described, in particular the previous method of analysis, an apparatus is preferentially used as illustrated in the FIGS. 7, 8 and 9. The apparatus (FIG. 7) contains an array of electrodes as in the prior art, but it is characterised by a main microchamber (CHM) and by a multiplicity of secondary microchambers (CHJ). The main microchamber may be filled with a sample comprising at least one cell through the respective inlets (IM1) and outlets (OM1). Each secondary microchamber (CHJ) is of larger dimensions, preferably substantially comparable to those of a cell, as shown in FIG. 7. Preferably each secondary microchamber is connected to the main microchamber through a channel (LCHG) with a configuration (length and/or shape) sufficient to prevent (avoid or at least limit) the dispersion of the sample by diffusion and contamination towards other microchambers, in the time necessary for the analysis. According to a possible variation (FIG. 8), there is a multiplicity of secondary microchambers for lysis (CHLJ) connected to a channel for capillary electrophoresis on chip, for example with a cross junction (TJ). Alternatively a series of channels for capillary electrophoresis may be produced with a double T junction, according to the prior art. Optionally, at the end of the channel for capillary electrophoresis there is an integrated sensor (SENS_J), of an impedenziometric and/or optical type, able to produce an electropherogram based on the migration time of the compounds analysed from the junction (cross or double T) to the sensor itself. A further variation is illustrated in FIG. 9, where each microchamber of said multiplicity is connected to a capillary for electrophoresis (CAPJ) through a fluid outlet (OJ) of each secondary microchamber.

The invention claimed is:

1. A method for selecting and processing of first particles sensitive to the application of an external stimulus and lysing at least one selected first particle, said first particles being suspended in a fluid, comprising the steps of:
a) providing an array of electrodes, each electrode having dimensions comparable to or smaller than those of said first particles and each electrode being a selectable electrode;
b) selectively energizing said array of electrodes to apply to all of said electrodes a first pattern of voltages to generate a first field of force having first points of stable equilibrium each positioned at a first position, wherein the first particles are attracted towards the first points of stable equilibrium and are situated at the first positions;
c) applying to all of said electrodes of said array a second pattern of voltages, different from the first pattern of voltages, to generate a second field of force having at least one second point of stable equilibrium positioned at a second position in a gap between at least two adjacent electrodes in proximity of the at least one selected first particle to be lysed; wherein the at least one selected first particle to be lysed is attracted to the at least one second point of stable equilibrium and shifted to the second position, wherein:
  i) said second field of force applies, only at the second position at which at least one second point of stable equilibrium is generated, a stimulus to lyse the at least one selected first particle to be lysed and said second field of force being designed such that at least one first particle that is not selected to be lysed remains at the first position;
  ii) said first pattern of voltages and said second pattern of voltages are applied in a time sequence to the same said electrodes;
d) after step c) applying again said first pattern of voltages to said electrodes; and
e) while step d) is in progress, producing a controlled shift of said fluid to recover a selected product of lysis of said at least one selected first particle.

2. The method according to claim 1, wherein said stimulus consists of a localised heating of a fluid in which said at least one selected first particle to be lysed is immersed.

3. The method according to claim 2, wherein said second pattern of voltages is such as to produce the selective heating by Joule effect at the second position at which said second stable point of stable equilibrium is generated.

4. The method according to claim 2, wherein said second pattern of voltages is generated in either AC or DC.

5. The method according to claim 1, wherein said first pattern of voltages for generating said first field of force presents a first amplitude and a first frequency; and in that said second pattern of voltages for generating the second field of force presents a second amplitude and a second frequency, at least one of which is different from said first amplitude and first frequency.

6. The method according to claim 5, wherein said stimulus consists of a force applicable to said at least one selected first particle to be lysed by said second field of force; said second pattern of voltages being generated in AC.

7. The method according to claim 6, wherein said at least one selected first particle to be lysed is a biological entity with a lysable membrane in which said stimulus consists of bringing the transmembrane potential of said at least one selected first particle to a value such as to produce the rupture of the membrane.

8. The method according to claim 1, further comprising checking the lysis of said at least one selected first particle to be lysed.

9. The method according to claim 1, wherein said first particles are suspended in a fluid, further comprising choosing the fluid to present a low electric conductivity compared to an electrical conductivity of physiological fluids.

10. A method for isolating interesting particles from a population of particles including said interesting particles and non-interesting particles, the population of particles being suspended in a fluid, comprising the steps of:
a) introducing said population of particles suspended in a fluid into a microchamber equipped with an array of electrodes, each electrode having dimensions identical with or smaller than those of particles of the population of particles including said interesting particles and each electrode being selectable;
b) selectively energizing said electrodes of the array of electrodes to apply to all of said electrodes a first pattern of voltages to generate a first field of force having first points of stable equilibrium each positioned a first position, wherein said interesting and non-interesting particles from the population of particles are attracted towards the first points of stable equilibrium and are situated at the first positions;

c) applying to all of said electrodes of said array of electrodes a second pattern of voltages, different from the first pattern of voltages, to generate a second field of force having second stable points of equilibrium each positioned at a second position arranged in a gap between adjacent electrodes of said array of electrodes in proximity of the non-interesting particles, wherein the non-interesting particles of said population of particles are attracted towards the second points of stable equilibrium and shifted to the second position and the interesting particles remain at the first positions, wherein
   i) said second field of force is applies solely at the second points of stable equilibrium a stimulus suitable to selectively lyse the non-interesting particles
   ii) said first and second pattern of voltages are applied in a time sequence to the same said first and second electrodes; and the method further comprising the step of
d) recovering the interesting particles, wherein recovering the particles comprises:
after step c) applying again said first pattern of voltages to said electrodes; and
while the reapplication of the first pattern of voltages to said electrodes is in progress, producing a controlled shift of said fluid to recover a selected product of lysis of the non-interesting particles.

11. The method according to claim 10, wherein said step c) is applied simultaneously and/or repeatedly to the non-interesting particles by applying to said first electrodes a plurality of voltage patterns suited to apply to said non-interesting particles stimuli of an intensity and/or type such as to produce the selective lysis of the non-interesting particles.

12. A method for the ultra-purification of interesting particles from non-interesting particles comprising contaminated particles, wherein the isolation method according to claim 10 is applied, where step c) is applied only to said contaminated particles.

13. A method for the analysis of particles, comprising:
a) introducing said particles, suspended in a fluid, into a microchamber;
b) shifting said particles, selectively, each into a predetermined point of analysis separate from said microchamber, but hydraulically connected to it;
c) applying to said particles present in said predetermined points of analysis a method according to claim 1;
d) applying a defined analysis protocol on site to the respective debris of the lysis of said particles.

14. The method according to claim 13, where said defined analysis protocol is chosen from the group including: polymerase chain reaction, capillary electrophoresis on chip; or combinations of polymerase chain reaction and capillary electrophoresis on chip.

15. A method for producing the fusion of first particles with second particles, in which the first and second particles are biological entities with a lysable membrane, and in which the membrane of said particles is sensitive to the application of an external stimulus, the first and second particles being suspended in a fluid comprising:
a) providing an array of electrodes, each electrode having dimensions identical with or smaller than those of said first and second particles and each electrode being selectable;

b) selectively energizing said electrodes of said array of electrodes to apply to all of said electrodes a first pattern of voltages to generate a first field force having first points of stable equilibrium, wherein the said first and second particles are attracted towards first points of stable equilibrium and situated at a first position in proximity of said first and second electrodes; and c) applying to all said electrodes of said array of electrodes a second pattern of voltages, different from the first pattern to generate a second field of force having at least one second point of stable equilibrium positioned at a second position in a gap between at least two adjacent electrodes of said array of electrodes in proximity to selected first and second particles; wherein the selected first and second particles are attracted to the at least one second point of stable equilibrium and shifted to the second position, wherein
   i) said second field of force applies solely at the at least one second stable point of equilibrium a stimulus suitable to fuse membranes of the selected first and second particles to be fused together,
   ii) said first and second patterns of voltages are applied in a time sequence to the same said first and second electrodes; and
d) after step c) applying again said first pattern of voltages to said electrodes; and
e) while step d) is in progress, producing a controlled shift of said fluid to recover the fused first and second particles.

16. The method according to claim 7, wherein said biological entity is a cell.

17. The method of claim 8, wherein said step of checking the lysis is carried out by a device with sensors integrated with said array of electrodes in a single chip.

18. A method for selection and processing of particles sensitive to an application of an external stimulus, comprising:
applying a first pattern of voltages to an array of electrodes to generate a first field of force having first points of stable equilibrium, wherein the particles are attracted towards the first points of stable equilibrium and reside at a first position and the particles comprise first particles to be ruptured or lysed and second particles;
applying a second pattern of voltages to the array of electrodes to generate a second field of force having second points of stable equilibrium each positioned at a second position between two adjacent electrodes, wherein the two adjacent electrodes are disposed in proximity to the first particles such that only the first particles are attracted to the second points of stable equilibrium and shifted the second position while the second particles remain at the first positions, wherein the second field of force generated by the second pattern of voltages is configured to also apply electric impulses between the two adjacent electrodes to apply a stimulus to the first particles in the second position suitable to rupture or lyse the first particles, wherein the first and second patterns of voltages are applied in a time sequence to the same electrodes;
applying again said first pattern of voltages to said electrodes; and
while the first pattern of voltages is being reapplied, producing a controlled shift of said fluid to recover a selected product of rupture or lysis of said at least one selected first particle.

* * * * *